(12) United States Patent
Ballou, Jr. et al.

(10) Patent No.: US 9,087,145 B2
(45) Date of Patent: Jul. 21, 2015

(54) OPHTHALMIC DRUG DELIVERY

(75) Inventors: Bernard L. Ballou, Jr., Raleigh, NC (US); Mark Packer, Eugene, OR (US); Russell John Mumper, Chapel Hill, NC (US); Tsontcho Inachulev, San Mateo, CA (US)

(73) Assignee: Eyenovia, Inc., Tampa, FL (US)

( * ) Notice: Subject to any disclaimer, the term of this patent is extended or adjusted under 35 U.S.C. 154(b) by 0 days.

(21) Appl. No.: 13/184,446

(22) Filed: Jul. 15, 2011

(65) Prior Publication Data

US 2012/0070467 A1 Mar. 22, 2012

Related U.S. Application Data

(60) Provisional application No. 61/400,864, filed on Jul. 15, 2010, provisional application No. 61/401,850, filed on Aug. 20, 2010, provisional application No. 61/401,920, filed on Aug. 20, 2010, provisional application No. 61/401,918, filed on Aug. 20, 2010, provisional application No. 61/401,848, filed on Aug. 20, 2010, provisional application No. 61/401,849, filed on Aug. 20, 2010, provisional application No. 61/462,576, filed on Feb. 4, 2011, provisional application No. 61/462,791, filed on Feb. 5, 2011, provisional application No. 61/463,280, filed on Feb. 15, 2011, provisional application No. 61/516,462, filed on Apr. 4, 2011, provisional application No. 61/516,496, filed on Apr. 4, 2011, provisional application No. 61/516,495, filed on Apr. 4, 2011, provisional application No. 61/516,694, filed on Apr. 6, 2011.

(51) Int. Cl.

| | |
|---|---|
| *A61F 9/00* | (2006.01) |
| *A61P 27/06* | (2006.01) |
| *A61P 31/04* | (2006.01) |
| *A61M 11/00* | (2006.01) |
| *A61M 35/00* | (2006.01) |
| *A61K 31/5377* | (2006.01) |
| *A61K 31/7036* | (2006.01) |
| *A61K 9/00* | (2006.01) |
| *B05B 17/00* | (2006.01) |
| *G06F 19/00* | (2011.01) |

(52) U.S. Cl.
CPC .............. *G06F 19/3406* (2013.01); *A61F 9/00* (2013.01); *A61F 9/0008* (2013.01); *A61M 11/00* (2013.01); *G06F 19/3418* (2013.01); *A61M 2210/0612* (2013.01); *G06F 19/322* (2013.01); *G06F 19/3456* (2013.01); *G06F 19/3487* (2013.01)

(58) Field of Classification Search
CPC .................... A61F 9/0008; A61M 2210/0612
See application file for complete search history.

(56) References Cited

U.S. PATENT DOCUMENTS

| | | | |
|---|---|---|---|
| 1,482,747 | A | 2/1924 | Howe |
| 1,988,637 | A | 1/1935 | Tinkham |
| 2,189,643 | A | 2/1940 | Ward |
| 2,200,008 | A | 5/1940 | Nowak |
| 2,249,608 | A | 7/1941 | Greene |
| 2,322,808 | A | 6/1943 | Hothersall |
| 2,552,857 | A | 5/1951 | Knapp |
| 2,595,317 | A | 5/1952 | White |
| 2,987,439 | A | 6/1961 | Wittlinger |
| 3,170,462 | A | 2/1965 | Hall |
| 3,187,757 | A | 6/1965 | Jones et al. |
| 3,237,809 | A | 3/1966 | Daragan et al. |
| 3,310,830 | A | 3/1967 | Gattone |
| 3,314,426 | A | 4/1967 | Caroll |
| 3,439,674 | A | 4/1969 | Lelicoff |
| 3,602,399 | A | 8/1971 | Litman et al. |
| 3,658,257 | A | 4/1972 | Rood |
| 3,709,235 | A | 1/1973 | Washburn et al. |
| 3,779,245 | A | 12/1973 | Windsor |
| 3,780,950 | A | 12/1973 | Brennan |
| 3,795,351 | A | 3/1974 | Lehmann |
| 3,812,854 | A | 5/1974 | Michaels et al. |
| 3,826,258 | A | 7/1974 | Abraham |
| 3,845,764 | A | 11/1974 | Windsor |
| 3,901,443 | A | 8/1975 | Mitsui et al. |
| 3,906,949 | A | 9/1975 | Holland |
| 3,913,575 | A | 10/1975 | Windsor |
| 3,934,585 | A | 1/1976 | Maurice |
| 4,002,168 | A | 1/1977 | Petterson |
| 4,012,798 | A | 3/1977 | Liautaud |
| 4,052,985 | A | 10/1977 | Coleman et al. |

(Continued)

FOREIGN PATENT DOCUMENTS

| | | |
|---|---|---|
| CA | 2451835 | 1/2003 |
| DE | 196 16 300 A1 | 10/1997 |

(Continued)

OTHER PUBLICATIONS

Santvliet et al, Survey of Ophthamology, Mar.-Apr. 2004, vol. 49, pp. 197-211.*

(Continued)

*Primary Examiner* — Brian-Yong Kwon
*Assistant Examiner* — Mark V Stevens
(74) *Attorney, Agent, or Firm* — Polsinelli PC

(57) ABSTRACT

The present invention includes and provides a method of delivering a medicament to an eye of a subject in need thereof a solution, the method comprising: (a) providing droplets containing the medicament with a specified average size and average initial ejecting velocity; and (b) delivering the medicament to the eye, where the droplets deliver a percentage of the ejected mass of the droplets to the eye.

38 Claims, No Drawings

(56) References Cited

U.S. PATENT DOCUMENTS

| | | |
|---|---|---|
| 4,067,499 A | 1/1978 | Cohen |
| 4,098,431 A | 7/1978 | Palmer et al. |
| D249,709 S | 9/1978 | Trovinger |
| 4,119,096 A | 10/1978 | Drews |
| 4,122,556 A | 10/1978 | Poler |
| 4,131,115 A | 12/1978 | Peng |
| 4,173,226 A | 11/1979 | Shell |
| 4,175,704 A | 11/1979 | Cohen |
| 4,175,706 A | 11/1979 | Gerstmann |
| 4,264,837 A | 4/1981 | Gaboriaud |
| 4,296,071 A | 10/1981 | Weiss et al. |
| 4,319,155 A | 3/1982 | Nakai et al. |
| 4,323,530 A | 4/1982 | Voss et al. |
| 4,338,936 A | 7/1982 | Nelson |
| 4,356,528 A | 10/1982 | Coffee |
| 4,381,533 A | 4/1983 | Coffee |
| 4,388,343 A | 6/1983 | Voss et al. |
| 4,390,542 A | 6/1983 | Schachar |
| 4,398,909 A | 8/1983 | Portnoff |
| 4,465,234 A | 8/1984 | Maehara et al. |
| 4,471,890 A | 9/1984 | Dougherty |
| 4,476,515 A | 10/1984 | Coffee |
| 4,479,609 A | 10/1984 | Maeda et al. |
| 4,493,119 A | 1/1985 | Baumann |
| 4,543,096 A | 9/1985 | Keene |
| 4,544,570 A | 10/1985 | Plunkett et al. |
| 4,564,016 A | 1/1986 | Maurice et al. |
| 4,580,721 A | 4/1986 | Coffee et al. |
| 4,605,167 A | 8/1986 | Maehara |
| 4,605,398 A | 8/1986 | Herrick |
| 4,627,845 A | 12/1986 | DeMotte |
| 4,641,384 A | 2/1987 | Landsberger et al. |
| 4,642,581 A | 2/1987 | Erickson |
| 4,658,290 A | 4/1987 | McKenna et al. |
| 4,659,014 A | 4/1987 | Soth et al. |
| 4,679,551 A | 7/1987 | Anthony |
| 4,685,906 A | 8/1987 | Murphy |
| 4,701,167 A | 10/1987 | Chekan |
| 4,702,418 A | 10/1987 | Carter et al. |
| 4,706,848 A | 11/1987 | D'Andrade |
| 4,740,206 A | 4/1988 | Allander |
| 4,742,713 A | 5/1988 | Abe et al. |
| 4,750,650 A | 6/1988 | Ling |
| 4,750,902 A | 6/1988 | Wuchinich et al. |
| 4,758,237 A | 7/1988 | Sacks |
| 4,758,727 A | 7/1988 | Tomei et al. |
| 4,759,755 A | 7/1988 | Hein et al. |
| 4,779,768 A | 10/1988 | St. Amand |
| 4,784,652 A | 11/1988 | Wikström |
| 4,790,479 A | 12/1988 | Matsumoto et al. |
| 4,792,334 A | 12/1988 | Py |
| 4,793,339 A | 12/1988 | Matsumoto et al. |
| 4,796,807 A | 1/1989 | Bendig et al. |
| 4,798,599 A | 1/1989 | Thomas |
| 4,809,914 A | 3/1989 | Goncalves |
| 4,815,661 A | 3/1989 | Anthony |
| 4,826,025 A | 5/1989 | Abiko et al. |
| 4,850,534 A | 7/1989 | Takahashi et al. |
| 4,863,073 A | 9/1989 | Burt et al. |
| 4,863,443 A | 9/1989 | Hornung |
| 4,863,457 A | 9/1989 | Lee |
| 4,871,091 A | 10/1989 | Preziosi |
| 4,877,989 A | 10/1989 | Drews et al. |
| 4,880,146 A | 11/1989 | Hudgins |
| 4,881,283 A | 11/1989 | Liautaud |
| 4,886,189 A | 12/1989 | Vanderjagt |
| 4,896,832 A | 1/1990 | Howlett |
| 4,908,024 A | 3/1990 | Py |
| 4,912,357 A | 3/1990 | Drews et al. |
| 4,917,274 A | 4/1990 | Asa et al. |
| 4,927,062 A | 5/1990 | Walsh |
| 4,927,115 A | 5/1990 | Bahroos et al. |
| 4,946,452 A | 8/1990 | Py |
| 4,952,212 A | 8/1990 | Booth et al. |
| 4,961,885 A | 10/1990 | Avrahami et al. |
| 4,969,869 A | 11/1990 | Burgin et al. |
| 4,981,479 A | 1/1991 | Py |
| 4,996,502 A | 2/1991 | Endo |
| 5,007,905 A | 4/1991 | Bauer |
| 5,019,037 A | 5/1991 | Wang et al. |
| 5,029,579 A | 7/1991 | Trammell |
| 5,030,214 A | 7/1991 | Spector |
| 5,032,111 A | 7/1991 | Morris et al. |
| 5,037,012 A | 8/1991 | Langford |
| 5,040,706 A | 8/1991 | Davis et al. |
| 5,047,009 A | 9/1991 | Morris et al. |
| 5,048,727 A | 9/1991 | Vlasich |
| 5,053,000 A | 10/1991 | Booth et al. |
| 5,054,477 A | 10/1991 | Terada et al. |
| 5,064,420 A | 11/1991 | Clarke et al. |
| 5,066,276 A | 11/1991 | Wang |
| 5,069,204 A | 12/1991 | Smith et al. |
| 5,069,675 A | 12/1991 | Menchel et al. |
| 5,085,651 A | 2/1992 | Py |
| 5,098,375 A | 3/1992 | Baier |
| 5,133,702 A | 7/1992 | Py |
| 5,134,993 A | 8/1992 | van der Linden et al. |
| 5,139,496 A | 8/1992 | Hed |
| 5,145,113 A | 9/1992 | Burwell et al. |
| 5,152,435 A | 10/1992 | Stand et al. |
| 5,152,456 A | 10/1992 | Ross et al. |
| 5,163,929 A | 11/1992 | Py |
| 5,164,740 A | 11/1992 | Ivri |
| 5,170,782 A | 12/1992 | Kocinski |
| 5,171,306 A | 12/1992 | Vo |
| 5,176,856 A | 1/1993 | Takahashi et al. |
| 5,193,745 A | 3/1993 | Holm |
| 5,201,726 A | 4/1993 | Kirkham |
| 5,203,506 A | 4/1993 | Gross et al. |
| 5,226,538 A | 7/1993 | Roselle |
| 5,252,318 A | 10/1993 | Joshi et al. |
| 5,259,385 A | 11/1993 | Miller et al. |
| 5,261,601 A | 11/1993 | Ross et al. |
| 5,265,288 A | 11/1993 | Allison |
| 5,267,986 A | 12/1993 | Py |
| 5,276,867 A | 1/1994 | Kenley et al. |
| 5,299,739 A | 4/1994 | Takahashi et al. |
| 5,316,159 A | 5/1994 | Douglas et al. |
| 5,318,014 A | 6/1994 | Carter |
| 5,320,845 A | 6/1994 | Py |
| 5,354,032 A | 10/1994 | Sims et al. |
| 5,364,405 A | 11/1994 | Zaleski |
| 5,368,582 A | 11/1994 | Bertera |
| 5,401,259 A | 3/1995 | Py |
| 5,405,614 A | 4/1995 | D'Angelo et al. |
| 5,431,663 A | 7/1995 | Carter |
| 5,435,282 A | 7/1995 | Haber et al. |
| 5,435,465 A | 7/1995 | El-Amin |
| 5,462,586 A | 10/1995 | Sugiyama et al. |
| 5,485,828 A | 1/1996 | Hauser |
| 5,496,411 A | 3/1996 | Candy |
| 5,499,751 A | 3/1996 | Meyer |
| D368,774 S | 4/1996 | Py |
| 5,515,841 A | 5/1996 | Robertson et al. |
| 5,518,179 A | 5/1996 | Humberstone et al. |
| 5,529,055 A | 6/1996 | Gueret |
| D374,719 S | 10/1996 | Py |
| 5,564,016 A | 10/1996 | Korenshtein |
| 5,584,823 A | 12/1996 | Valberg |
| 5,586,550 A | 12/1996 | Ivri et al. |
| 5,588,564 A | 12/1996 | Hutson et al. |
| 5,607,410 A | 3/1997 | Branch |
| 5,613,957 A | 3/1997 | Py |
| 5,614,545 A | 3/1997 | Martin et al. |
| 5,630,793 A * | 5/1997 | Rowe .............................. 604/20 |
| 5,657,926 A | 8/1997 | Toda |
| 5,665,079 A | 9/1997 | Stahl |
| 5,685,869 A | 11/1997 | Py |
| 5,687,874 A | 11/1997 | Omori et al. |
| 5,707,636 A | 1/1998 | Rodriguez et al. |
| 5,724,021 A | 3/1998 | Perrone |
| 5,730,723 A | 3/1998 | Castellano et al. |
| 5,735,811 A | 4/1998 | Brisken |
| 5,740,947 A | 4/1998 | Flaig et al. |

(56) References Cited

U.S. PATENT DOCUMENTS

| | | |
|---|---|---|
| 5,746,728 A | 5/1998 | Py |
| 5,758,637 A | 6/1998 | Ivri et al. |
| 5,803,106 A | 9/1998 | Cohen et al. |
| 5,807,357 A | 9/1998 | Kang |
| 5,823,428 A | 10/1998 | Humberstone et al. |
| 5,838,350 A | 11/1998 | Newcombe et al. |
| 5,843,109 A | 12/1998 | Mehta et al. |
| 5,855,322 A | 1/1999 | Py |
| 5,881,956 A | 3/1999 | Cohen et al. |
| 5,893,515 A | 4/1999 | Hahn et al. |
| 5,894,841 A | 4/1999 | Voges |
| 5,938,117 A | 8/1999 | Ivri |
| D413,668 S | 9/1999 | Mannberg et al. |
| 5,957,943 A | 9/1999 | Vaitekunas |
| 5,970,974 A | 10/1999 | Van Der Linden et al. |
| 5,996,903 A | 12/1999 | Asai et al. |
| 5,997,518 A | 12/1999 | Laibovitz et al. |
| 6,008,468 A | 12/1999 | Tanaka et al. |
| 6,011,062 A * | 1/2000 | Schneider et al. ............ 514/530 |
| 6,027,450 A | 2/2000 | Brown |
| 6,039,565 A | 3/2000 | Chou et al. |
| 6,062,212 A | 5/2000 | Davison et al. |
| 6,083,922 A | 7/2000 | Montgomery |
| 6,085,740 A | 7/2000 | Ivri et al. |
| 6,135,427 A | 10/2000 | Tsai |
| 6,152,383 A | 11/2000 | Chen |
| 6,159,188 A | 12/2000 | Laibovitz et al. |
| 6,193,683 B1 | 2/2001 | Ludin et al. |
| 6,203,759 B1 | 3/2001 | Pelc et al. |
| 6,216,966 B1 | 4/2001 | Prendergast et al. |
| 6,221,038 B1 | 4/2001 | Brisken |
| 6,228,046 B1 | 5/2001 | Brisken |
| 6,235,024 B1 | 5/2001 | Tu |
| 6,254,579 B1 | 7/2001 | Cogger et al. |
| 6,254,587 B1 | 7/2001 | Christ et al. |
| 6,263,872 B1 | 7/2001 | Schuster et al. |
| 6,273,342 B1 | 8/2001 | Terada et al. |
| 6,296,626 B1 | 10/2001 | Stein |
| 6,318,361 B1 | 11/2001 | Sosiak |
| 6,336,917 B1 | 1/2002 | Berke |
| 6,341,732 B1 | 1/2002 | Martin et al. |
| 6,357,442 B1 | 3/2002 | Casper et al. |
| 6,357,671 B1 | 3/2002 | Cewers |
| 6,367,685 B1 | 4/2002 | Jiang et al. |
| 6,394,363 B1 | 5/2002 | Arnott et al. |
| 6,398,737 B2 | 6/2002 | Moore et al. |
| 6,398,766 B1 | 6/2002 | Branch |
| 6,422,431 B2 | 7/2002 | Pelc et al. |
| 6,423,040 B1 | 7/2002 | Benktzon et al. |
| 6,425,888 B1 | 7/2002 | Embleton et al. |
| 6,427,682 B1 | 8/2002 | Klimowicz et al. |
| 6,442,423 B1 | 8/2002 | Domb et al. |
| 6,443,146 B1 | 9/2002 | Voges |
| 6,467,476 B1 | 10/2002 | Ivri et al. |
| 6,524,287 B1 | 2/2003 | Cogger |
| 6,526,976 B1 | 3/2003 | Baran |
| 6,530,370 B1 | 3/2003 | Heinonen |
| 6,540,153 B1 | 4/2003 | Ivri |
| 6,540,154 B1 | 4/2003 | Ivri et al. |
| 6,543,443 B1 | 4/2003 | Klimowicz et al. |
| 6,546,927 B2 | 4/2003 | Litherland et al. |
| 6,550,472 B2 | 4/2003 | Litherland et al. |
| 6,554,201 B2 | 4/2003 | Klimowicz et al. |
| 6,554,801 B1 | 4/2003 | Steward et al. |
| 6,569,131 B1 | 5/2003 | Michael et al. |
| 6,569,387 B1 | 5/2003 | Furner et al. |
| 6,601,581 B1 | 8/2003 | Babaev |
| 6,610,033 B1 | 8/2003 | Melanson et al. |
| 6,612,302 B1 | 9/2003 | Rand |
| 6,615,824 B2 | 9/2003 | Power |
| 6,619,562 B2 | 9/2003 | Hamaguchi et al. |
| 6,622,720 B2 | 9/2003 | Hadimioglu |
| 6,629,646 B1 | 10/2003 | Ivri |
| 6,640,804 B2 | 11/2003 | Ivri et al. |
| 6,650,935 B1 | 11/2003 | Watmough |
| 6,651,650 B1 | 11/2003 | Yamamoto et al. |
| 6,659,364 B1 | 12/2003 | Humberstone et al. |
| 6,669,961 B2 | 12/2003 | Kim et al. |
| 6,676,034 B2 | 1/2004 | Tanaka et al. |
| 6,679,436 B1 | 1/2004 | Onishi et al. |
| 6,684,681 B1 | 2/2004 | Zombo |
| 6,684,879 B1 | 2/2004 | Coffee et al. |
| 6,719,770 B2 | 4/2004 | Laufer et al. |
| 6,732,944 B2 | 5/2004 | Litherland et al. |
| 6,736,904 B2 | 5/2004 | Poniatowski et al. |
| 6,740,107 B2 | 5/2004 | Loeb et al. |
| 6,748,944 B1 | 6/2004 | Della Vecchia et al. |
| 6,761,286 B2 | 7/2004 | Py et al. |
| 6,789,741 B2 | 9/2004 | Varanasi et al. |
| 6,814,071 B2 | 11/2004 | Klimowicz et al. |
| 6,851,626 B2 | 2/2005 | Patel et al. |
| 6,854,662 B2 | 2/2005 | Chen |
| 6,863,224 B2 | 3/2005 | Terada et al. |
| 6,877,642 B1 | 4/2005 | Maddox et al. |
| 6,885,818 B2 | 4/2005 | Goldstein |
| 6,901,926 B2 | 6/2005 | Yamamoto et al. |
| 6,913,205 B2 | 7/2005 | Cornet et al. |
| 6,921,020 B2 | 7/2005 | Ivri |
| 6,926,208 B2 | 8/2005 | Ivri |
| 6,946,117 B1 | 9/2005 | Schutt et al. |
| 6,964,647 B1 | 11/2005 | Babaev |
| 6,969,165 B2 | 11/2005 | Olsen |
| 6,974,450 B2 | 12/2005 | Weber et al. |
| 6,976,279 B1 | 12/2005 | Berke et al. |
| 6,976,969 B2 | 12/2005 | Messerly |
| 6,978,945 B2 | 12/2005 | Wong et al. |
| 7,017,573 B1 | 3/2006 | Rasor et al. |
| 7,032,590 B2 | 4/2006 | Loeffler et al. |
| 7,040,549 B2 | 5/2006 | Ivri et al. |
| 7,066,398 B2 | 6/2006 | Borland et al. |
| 7,081,757 B2 | 7/2006 | Unsworth et al. |
| 7,083,112 B2 | 8/2006 | Ivri |
| 7,104,463 B2 | 9/2006 | Litherland et al. |
| 7,108,197 B2 | 9/2006 | Ivri |
| 7,121,275 B2 | 10/2006 | Noolandi et al. |
| D533,658 S | 12/2006 | Collins, Jr. et al. |
| 7,153,315 B2 | 12/2006 | Miller |
| 7,161,269 B2 | 1/2007 | Kayama et al. |
| 7,168,633 B2 | 1/2007 | Wang et al. |
| D537,160 S | 2/2007 | Lowell |
| 7,174,888 B2 | 2/2007 | Ivri et al. |
| 7,192,129 B2 | 3/2007 | Droege et al. |
| 7,201,732 B2 | 4/2007 | Anderson et al. |
| 7,204,820 B2 | 4/2007 | Akahoshi |
| 7,229,028 B2 | 6/2007 | Chen et al. |
| 7,234,460 B2 | 6/2007 | Greenleaf et al. |
| 7,314,187 B2 | 1/2008 | Hochrainer et al. |
| 7,316,067 B2 | 1/2008 | Blakey |
| 7,331,339 B2 | 2/2008 | Smith et al. |
| 7,357,133 B2 | 4/2008 | Goodchild |
| 7,472,701 B2 | 1/2009 | Pfichner et al. |
| D597,206 S | 7/2009 | Collins, Jr. et al. |
| 7,574,787 B2 | 8/2009 | Xu et al. |
| 7,678,089 B2 | 3/2010 | Py et al. |
| 7,712,466 B2 | 5/2010 | Addington et al. |
| 7,819,115 B2 | 10/2010 | Sexton et al. |
| 7,883,031 B2 | 2/2011 | Collins, Jr. et al. |
| 8,012,136 B2 | 9/2011 | Collins, Jr. et al. |
| 2001/0025190 A1 | 9/2001 | Weber et al. |
| 2001/0049608 A1 | 12/2001 | Hochman |
| 2001/0056258 A1 | 12/2001 | Evans |
| 2002/0016576 A1 | 2/2002 | Lee |
| 2002/0039502 A1 | 4/2002 | Matsumoto et al. |
| 2002/0043262 A1 | 4/2002 | Langford et al. |
| 2002/0073989 A1 | 6/2002 | Hadimioglu |
| 2002/0074362 A1 | 6/2002 | Py et al. |
| 2002/0107492 A1 | 8/2002 | Brach et al. |
| 2002/0121285 A1 | 9/2002 | Poniatowski et al. |
| 2002/0124843 A1 | 9/2002 | Skiba et al. |
| 2002/0161344 A1 | 10/2002 | Peclat et al. |
| 2003/0032930 A1 | 2/2003 | Branch |
| 2003/0078551 A1 | 4/2003 | Hochrainer et al. |
| 2003/0114901 A1 | 6/2003 | Loeb et al. |
| 2003/0144594 A1 | 7/2003 | Gellman |

(56) References Cited

U.S. PATENT DOCUMENTS

| | | |
|---|---|---|
| 2003/0185892 A1 | 10/2003 | Bell et al. |
| 2003/0192532 A1 | 10/2003 | Hopkins |
| 2004/0010239 A1 | 1/2004 | Hochrainer et al. |
| 2004/0039355 A1 | 2/2004 | Gonzalez et al. |
| 2004/0045547 A1 | 3/2004 | Yamamoto et al. |
| 2004/0050953 A1 | 3/2004 | Terada et al. |
| 2004/0082884 A1 | 4/2004 | Pal et al. |
| 2004/0164099 A1 | 8/2004 | Diestelhorst et al. |
| 2004/0176757 A1 | 9/2004 | Sinelnikov et al. |
| 2004/0186384 A1 | 9/2004 | Babaev |
| 2004/0204674 A1 | 10/2004 | Anderson et al. |
| 2004/0215157 A1* | 10/2004 | Peclat et al. .................. 604/294 |
| 2004/0220537 A1 | 11/2004 | Embleton et al. |
| 2004/0256487 A1 | 12/2004 | Collins, Jr. et al. |
| 2005/0001981 A1 | 1/2005 | Anderson et al. |
| 2005/0029307 A1 | 2/2005 | Py et al. |
| 2005/0077315 A1 | 4/2005 | Pavlu et al. |
| 2005/0077392 A1 | 4/2005 | Geser et al. |
| 2005/0089545 A1 | 4/2005 | Kuwano et al. |
| 2005/0195598 A1 | 9/2005 | Dancs et al. |
| 2005/0199236 A1 | 9/2005 | Fink et al. |
| 2005/0240162 A1 | 10/2005 | Chen et al. |
| 2005/0244339 A1 | 11/2005 | Jauernig et al. |
| 2005/0261641 A1 | 11/2005 | Warchol et al. |
| 2005/0263608 A1 | 12/2005 | Ivri |
| 2005/0275310 A1 | 12/2005 | Ripoll |
| 2005/0279350 A1 | 12/2005 | Rasor et al. |
| 2006/0024374 A1 | 2/2006 | Gasco et al. |
| 2006/0057216 A1 | 3/2006 | Salamone et al. |
| 2006/0174869 A1 | 8/2006 | Gumaste et al. |
| 2006/0196518 A1 | 9/2006 | Hon |
| 2006/0201501 A1 | 9/2006 | Morrison et al. |
| 2006/0209129 A1 | 9/2006 | Onozawa |
| 2006/0213503 A1 | 9/2006 | Borgschulte et al. |
| 2006/0258993 A1 | 11/2006 | Hochrainer et al. |
| 2007/0023547 A1 | 2/2007 | Borland et al. |
| 2007/0044792 A1 | 3/2007 | Ivri |
| 2007/0113841 A1 | 5/2007 | Fuchs |
| 2007/0119968 A1 | 5/2007 | Collins, Jr. et al. |
| 2007/0119969 A1 | 5/2007 | Collins, Jr. et al. |
| 2007/0211212 A1 | 9/2007 | Bennwik |
| 2008/0017189 A1 | 1/2008 | Ruckdeschel et al. |
| 2008/0097359 A1 | 4/2008 | Hochrainer et al. |
| 2008/0142624 A1 | 6/2008 | Ivri et al. |
| 2008/0164339 A1 | 7/2008 | Duru |
| 2008/0233053 A1 | 9/2008 | Gross et al. |
| 2008/0299049 A1 | 12/2008 | Stangl |
| 2008/0303850 A1 | 12/2008 | Shin et al. |
| 2008/0308096 A1 | 12/2008 | Borgschulte et al. |
| 2009/0025713 A1 | 1/2009 | Keller et al. |
| 2009/0114742 A1 | 5/2009 | Collins, Jr. |
| 2009/0149829 A1 | 6/2009 | Collins, Jr. |
| 2009/0192443 A1 | 7/2009 | Collins, Jr. et al. |
| 2009/0212133 A1 | 8/2009 | Collins, Jr. et al. |
| 2010/0044460 A1 | 2/2010 | Sauzade |
| 2010/0211408 A1 | 8/2010 | Park et al. |
| 2010/0222752 A1 | 9/2010 | Collins, Jr. |
| 2010/0283601 A1 | 11/2010 | Tai et al. |

FOREIGN PATENT DOCUMENTS

| | | |
|---|---|---|
| DE | 19616300 A1 | 10/1997 |
| DE | 199 34 582 A1 | 1/2001 |
| EP | 0 011 269 A1 | 5/1980 |
| EP | 0 150 571 A1 | 8/1985 |
| EP | 0 224 352 A1 | 6/1987 |
| EP | 0 389 665 A1 | 10/1990 |
| EP | 0 590 165 A1 | 4/1994 |
| EP | 0 823 246 A2 | 2/1996 |
| EP | 0 933 138 A2 | 8/1999 |
| EP | 1 493 410 A2 | 1/2005 |
| EP | 1493410 A2 | 1/2005 |
| FR | 1 271 341 | 7/1961 |
| GB | 558866 | 7/1942 |
| GB | 1 569 707 | 7/1980 |
| JP | 8-52193 | 2/1996 |
| JP | U3104861 | 4/2004 |
| TW | 1293898 | 7/1994 |
| WO | WO 85/00761 A1 | 2/1985 |
| WO | WO 91/12687 A1 | 8/1991 |
| WO | WO 91/14468 A1 | 10/1991 |
| WO | WO 94/13305 A1 | 6/1994 |
| WO | WO 94/23788 A1 | 10/1994 |
| WO | WO 95/26236 | 10/1995 |
| WO | WO 96/06581 | 3/1996 |
| WO | WO 97/05960 A1 | 2/1997 |
| WO | WO 97/12687 A1 | 4/1997 |
| WO | WO 97/23177 | 7/1997 |
| WO | WO 98/19383 A1 | 5/1998 |
| WO | WO 99/17888 A1 | 4/1999 |
| WO | WO 00/18455 A1 | 4/2000 |
| WO | WO 00/66277 A1 | 11/2000 |
| WO | WO 01/03645 A2 | 1/2001 |
| WO | WO 01/19437 A1 | 3/2001 |
| WO | WO 01/58236 A2 | 8/2001 |
| WO | WO 01/85245 A1 | 11/2001 |
| WO | WO 02/28545 A1 | 4/2002 |
| WO | WO 02/055131 A2 | 7/2002 |
| WO | 02/062488 A1 | 8/2002 |
| WO | WO 02/062488 A1 | 8/2002 |
| WO | WO 02/072169 A2 | 9/2002 |
| WO | WO 03/002045 A1 | 1/2003 |
| WO | WO 03/002265 A1 | 1/2003 |
| WO | WO 03/026556 A2 | 4/2003 |
| WO | 2004/028420 A1 | 4/2004 |
| WO | WO 2004/028420 A1 | 4/2004 |
| WO | WO 2004/050065 A1 | 6/2004 |
| WO | WO 2004/103478 A1 | 12/2004 |
| WO | WO 2004/105864 A1 | 12/2004 |
| WO | WO 2006/006963 A2 | 1/2006 |
| WO | WO 2006/082588 A2 | 8/2006 |
| WO | WO 03/097139 A1 | 11/2006 |
| WO | WO 2008/015394 A1 | 2/2008 |
| WO | 2009/148345 A2 | 12/2009 |
| WO | WO 2009/148345 A2 | 12/2009 |
| WO | WO 2012/009702 A1 | 1/2012 |
| WO | WO 2012/009706 A1 | 1/2012 |

OTHER PUBLICATIONS

Brown et al, Journal of the Society of Cosmetic Chemists, 1965, vol. 16, pp. 369-393.*

"Alcon®: Sharing One Vision," 2009 Annual Report, 46 pages (2009).

Conover (Ed.),"View into the Future of Ophthalmology Treatments," *Healthcare Observer*, 1(8):2-37 (2009).

Dhand, "Nebulizers That Use a Vibrating Mesh or Plate with Multiple Apertures to Generate Aerosol," *Respir Care*, 47(12):1406-1418 (2002).

Donnelly et al., "Using ultrasonic atomization to produce an aerosol of micron-scale particles," *Review of Scientific Instruments*, 76:113301-1-113301-10 (2005).

Durnam et al., "Gold-Chlorine and Gold-Bromine Equilibria in Fused Salts," *The Journal of Physical Chemistry*, 68(4):847-850 (1964).

Galambos et al., "Drop ejection utilizing sideways actuation of a MEMS piston," *Sensors and Actuators A*, 141:182-191 (2008).

Hinds, *Aerosol Technology: Properies, Behavior, and Measurement of Airborne Particles*, pp. 42-71, 111-119, & 294-301 (1999).

Instruction Manual for Omron® Model NE-U03V MicroAir® Nebulizer, 20 pages (No date).

International Search Report mailed Dec. 12, 2011, in International Application No. PCT/US2011/044291.

International Search Report mailed Dec. 13, 2011, in International Application No. PCT/US2011/044286.

Product Description for Xalatan®: latanoprost opthalmic solution, Pfizer Manufacturing, Belgium, NV, 8 pages (2009).

Quigley, "Improving Eye Drop Treatment for Glaucoma through Better Adherence," *Optometry and Vision Science*, 85(6):374-375 (2008).

(56) References Cited

OTHER PUBLICATIONS

Ranade et al., "Chapter seven: Intranasal and ocular drug delivery," *Drug Delivery Systems: Second Edition*, CLC Press, 39 pages (2004).
Rosen et al., "Printing High Viscosity Fluids Using Ultrasonic Droplet Generation," The George W. Woodruff School of Mechanical Engineering, Georgia Institute of Technology, pp. 239-253 (2008).
Shidhaye et al., "Novel drug delivery devices," *Pharma Times*, 38(7):24-27 (2006).
Tamilvanan et al., "The potential of lipid emulsion for ocular delivery of lipophilic drugs," *European Journal of Pharmaceutics and Biopharmaceutics*, 58:357-368 (2004).
Xia et al., "A potential application of a piezoelectric atomiser for opthalmic drug delivery," *BOB*, 4(1):9-17 (2007).
Yee et al., "Trends in Glaucoma Treatment," EyeWorld Educational Symposium, San Francisco, 8 pages (2006).
Yuan et al., "MEMS-based piezoelectric array microjet," *Microelectronic Engineering*, 66:767-772 (2003).

* cited by examiner

OPHTHALMIC DRUG DELIVERY

RELATED APPLICATIONS

The present application claims the benefit of the filing date of U.S. Provisional Application No. 61/400,864, filed Jul. 15, 2010, U.S. Provisional Application No. 61/401,850, filed Aug. 20, 2010, U.S. Provisional Application No. 61/401,920 filed Aug. 20, 2010, U.S. Provisional Application No. 61/401,918 filed Aug. 20, 2010, U.S. Provisional Application No. 61/401,848 filed Aug. 20, 2010, U.S. Provisional Application No. 61/401,849 filed Aug. 20, 2010, U.S. Provisional Application No. 61/462,576 filed Feb. 4, 2011, U.S. Provisional Application No. 61/462,791 filed Feb. 5, 2011, U.S. Provisional Application No. 61/463,280 filed Feb. 15, 2011, U.S. Provisional Application No. 61/516,462, filed Apr. 4, 2011, U.S. Provisional Application No. 61/516,496 filed Apr. 4, 2011, U.S. Provisional Application No. 61/516,495 filed Apr. 4, 2011, and U.S. Provisional Application No. 61/516,694, filed Apr. 6, 2011, the entire contents of each of which is specifically hereby incorporated by reference for all purposes. The present application is also related to U.S. Provisional Application No. 61/396,531 filed May 28, 2010, the entire contents of which is specifically hereby incorporated by reference for all purposes.

FIELD OF THE INVENTION

The present invention relates to devices for the generation of ejected droplets, methods of administration and uses thereof, and medicament compositions formulated therefor.

BACKGROUND OF THE INVENTION

A typical medical droplet as dispensed by an eye dropper bottle can vary, depending on the viscosity and surface tension of the fluid. In order to control the amount of active ingredient that is administered in a single droplet, the concentration of the active ingredient is adjusted by volume. Once the concentration is defined, a correct dosage may require one drop or more. However, since the human eye can typically retain only 7 μl of fluid at a time, even a single medical droplet can result in overflow and loss of part of the medication from the eye. Multiple drop dosage often compounds the problem of medication retention in the eye. Subjects will typically administer all droplets required for a dosage in one sitting, which exacerbates the problem and can result in 50 to 90% of the medication overflowing and leaking out of the eye.

Another further problem is that a single droplet of the defined concentration marks the lower limit of a dose and, as such, the amount of active ingredient that can be administered at the defined concentration. For example, pediatric application where lower doses are often advisable are an illustration of where the size/dose of a droplet can be problematic.

Given the above and other limitations of current ophthalmic delivery, a need exists for an efficient delivery system for solutions to the eye, including solutions containing medicaments.

SUMMARY OF THE INVENTION

To address such needs and others, provided herein are stable medicament compositions and uses thereof.

One embodiment provides a method of delivering a medicament to an eye of a subject in need thereof a solution, the method comprising: (a) providing droplets containing the medicament, where said droplets have an average drop size of between about 15 microns and about 100 microns in diameters and an average ejecting velocity of between about 0.5 m/s to about 20 m/s; and (b) delivering the medicament to the eye, where between about 80% to about 100% of the ejected mass of the droplets are deposited on the eye.

Another embodiment provides a method of delivering a medicament solution to a subject in need thereof by controlling droplet size and droplet deposit parameters of the medicament solution, the method comprising: (a) determining desired dosage of the medicament solution for the subject in need thereof; and (b) providing the desired dosage in a single application by determining the droplet size and deposit parameters.

Yet another embodiment provides a method for providing a solution to the eye, the method comprising: (a) providing droplets containing the medicament, having an average droplet size of between about 15 microns and about 100 microns in diameter and an average initial ejecting velocity of between about 0.5 m/s to about 20 m/s; and (b) delivering the medicament to the eye, where between about 80% to about 100% of the ejected mass of the droplets are deposited on the eye.

These and other aspects of the invention will become apparent to one of skill in the art.

DETAILED DESCRIPTION OF THE INVENTION

A. Methods of Generating Ejected Droplets

The present invention provides an effective approach to undertake dosing strategies. Dosing strategies also will incorporate various approaches to initiating treatment, stopping treatment, switching treatment and responding to different subject states.

Examples of dosing modes or strategies include night time administration, administration before waking, increased administration one week a month, three times a day, continuous dosing, bolus dosing, taper dosing, need-based dosing, and feedback dosing by the physician, provider, subject or family. The clinical scenarios where these can be employed include chronic disease, disease exacerbation, need for suppression treatment, need for recurrence treatment, or state of treatment like medicament tolerance.

B. Methods of Delivery and Treatment

Provided is a method of delivering a medicament to an eye of a subject in need thereof a solution, the method comprising: (a) providing droplets containing the medicament with a specified average size and average initial ejecting velocity; and (b) delivering the medicament to the eye, where the droplets deliver a percentage of the ejected mass of the droplets to the eye.

Devices capable of providing and delivering a fluid such as ophthalmic fluid to the eye are provided. In certain aspects, ejection devices include an ejection assembly which generates or provides a controllable stream of droplets of fluid. Fluids include, without limitation, suspensions and emulsions which have viscosity in a range capable of droplet formation using an ejector mechanism. As explained in further detail herein, in accordance with certain aspects of the present disclosure, the actuator mechanism may form a directed stream of droplets, which may be directed toward a target. The droplets will be formed in distribution of sizes, each distribution having an average droplet size. The average droplet size may be in the range of about 15 microns to about 100 microns, about 20 microns to about 100 microns, greater than 20 microns to about 100 microns, about 20 microns to about 80 microns, about 25 microns to about 75 microns, about 30 microns to about 60 microns, about 35 microns to about 55 microns, etc. However, the average droplet size may be as large as 2500 microns, depending on the intended application. Further, the droplets may have an average initial ejecting velocity of about 0.5 m/s to about 20 m/s, e.g., about 1 m/s to about 10 m/s, about 1 m/s to about 5 m/s, about 1 m/s to about 4 m/s, about 2 m/s, etc. As used herein, the ejecting size and the ejecting initial velocity are the size and velocity of the droplets when the droplets leave the ejector plate. The stream of droplets directed at a target will result in deposition of a percentage of the mass of the droplets including their composition onto the desired location.

The disclosed technology will eject droplets without substantial evaporation, entrainment of air, or deflection off the eye surface, which facilitates consistent dosing. Average ejecting droplet size and average initial ejecting velocity are dependent on factors including fluid viscosity, surface tension, ejector plate properties, geometry, and dimensions, as well as operating parameters of the piezoelectric actuator including its drive frequency. In some implementations, about 60% to about 100%, about 65% to about 100%, about 75% to about 100%, about 80% to about 100%, about 85% to about 100%, about 90% to about 100%, about 95% to about 100%, etc., of the ejected mass of droplets are deposited on the surface of the eye, such deposition being repeatable independent of operating and use conditions. The direction of flow of the stream of droplets may be horizontal, or any direction a user chooses to aim the actuation mechanism during use.

Droplet performance is generally related to particle diameter. Without intending to be limited, ejected droplets are slowed to a stop by air drag (i.e., stopping distance of the ejected droplets). Ejected droplets also fall vertically due to gravity. After a short acceleration time, the droplets reach terminal velocity where the drag force equals the force of gravity. The ejected droplets may carry air along with them, which creates an entrained airstream, which aids to then carry the ejected droplets beyond the calculated stopping distance. However, increased levels of entrained air may cause the ejected droplets to flow across an impact surface (e.g., an eye surface) because the entrained airflow must turn 90 degrees at such a surface. Small, ejected droplets (e.g., droplets having an average diameter less than about 17 microns, less than about 15 microns, etc.) are carried along the surface of the eye by the airstream and may not impact the surface. Contrasted to this, larger ejected droplets create less entrained air than an equivalent mass of smaller droplets, and have enough momentum to impact the surface. The ejected droplet stopping distance is a measure of this effect.

Also provided is a method of delivering a medicament solution to a subject in need thereof by controlling droplet size and deposit parameters of the medicament solution, the method comprising: (a) determining desired dosage of the medicament solution for the subject in need thereof; and (b) providing the desired dosage in a single application or multiple applications by determining the droplet size and deposit parameters.

Many factors, including those described herein, can influence the desired dosage. Once the desired dosage is determined, and also if desired frequency, such doses can be delivered. Frequency of dosing can vary by number of times, periodicity or both.

Also provided is a method for providing a solution to the eye, the method comprising: (a) providing droplets containing the solution, where the droplets have an average drop size in diameter and an average initial ejecting velocity; and (b) delivering the solution to the eye, where between about 80% to about 100% of the ejected mass of the droplets are deposited on the eye.

Further provided is a method of treating eye condition disorders, including glaucoma, infection or other eye indications, and related discomforts or other need in a subject in need thereof, the method comprising: (a) providing droplets containing said medicament with a specified average size and average initial ejecting velocity; and (b) delivering the medicament to the eye, where the droplets deliver a percentage of the ejected mass of the droplets to the eye.

Further provided is a method of providing a reduced dosage form of a medicament to an eye comprising: (a) providing droplets containing the medicament, where the droplets have an average drop size and an average initial ejecting velocity; and (b) delivering the medicament to the eye, where the droplets deliver a specified deposited mass of the droplets. In this or other aspects, the droplets can provide a total volume of less than 30 μl, 20 μl, 15 μl, 10 μl, 5 μl or 2 μl to eye.

C. Ejector Device

Exemplary ejector devices capable of generating droplets of the type described herein are provided in U.S. Patent Publication No. 2012/0143152, filed concurrently herewith, entitled "Drop-Generating Device", herein incorporated by reference in its entirety. In one aspect of one such device an ejector plate is coupled to an actuator. The manner and location of attachment of the actuator to the plate affects the operation of the ejection assembly and the creation of the droplet stream with the option of the actuator being a piezoelectric actuator.

As described in U.S. Patent Publication No. 2012/0143152, again herein incorporated by reference in its entirety, the ejector device may generally be an ejector device for delivering a fluid to an eye of a subject. For instance, the ejector device may comprise: a housing; a reservoir disposed within the housing for receiving a volume of ophthalmic fluid; and an ejector mechanism configured to eject a stream of droplets to the eye of a subject upon activation of the device by a user. The ejected stream of droplets may have an average ejected droplet diameter greater than 15 microns and a low entrained airflow such that the ejected stream of droplets is deposit on the eye of the subject during use. In certain embodiments, the ejector device includes a piezoelectric ejector mechanism comprising an ejector plate having a first surface coupled to a fluid delivery area of the reservoir and including a plurality of openings formed through its thickness, and a piezoelectric actuator coupled to a second surface of the ejector plate, the piezoelectric actuator operable to oscillate the ejector plate at a frequency and generate the ejected stream of droplets.

D. Medicament and Other Compositions

Any medicament showing a desired ophthalmic activity may be administered. In an aspect, the medicament is available by prescription. In another aspect, the medicament is available over-the-counter. In an aspect, the medicament is or comprises a biologic agent. In an aspect, the biologic agent is selected from the group consisting of a full-length antibody, an active fragment of a full-length antibody, a peptide, a pegylated peptide, and an enzymatic ingredient. In another aspect, the biologic ingredient is selected from the group consisting of bevacizumab, ranibizumab, FV fragments, bispecific antibodies, fusion molecules, pegaptanib, plasmin and microplasmin. In a further aspect, the biologic agent is selected from the group consisting of ranibizumab antibody FAB (including Lucentis™), VEGF Trap fusion molecule (including VEGF Trap-Eye™), microplasmin enzyme (including Ocriplasmin™), macugen pegylated polypeptide (including Pegaptanib™), and bevacizumab (including Avastin™).

In another aspect, a medicament to be administered is or comprises a small molecule. In an aspect, the medicament to be administered comprises a medicament selected from the group consisting of cyclosporine, neomycin, biomonidine, and aminoglycoside antibiotics, including, for example, tobramycin and gentamycin.

In various aspects, a solution may have different salinity. Salinity may be measured using a hydrometer. In various aspects, salinity may range from 0%, or a pure aqueous solution, to 2.5%. In other aspects, salinity may range from about 0.1% to about 1%, from about 0.5% to about 1%, from about 0.7% to about 1%, from about 0.8% to about 1%. In further aspects, salinity of a medicament may be about 0.1%, 0.2%, 0.3%, 0.4%, 0.5%, 0.6%, 0.7%, 0.8%, 0.9%, 1%, 1.1%, 1.2%, 1.3%, 1.4%, or about 1.5%. In other aspects, salinity may be less than about 1.5%, less than about 1%, less than about 0.5% or less than about 0.2%. In an aspect, the solution is isotonic with the site of delivery. For example, in various aspects, the medicament may be isotonic with human tears, blood, or eye tissue.

In an aspect, the medicament to be delivered comprises a medicament selected from the group consisting of carboxymethylcellulose sodium, tetrahydrozoline HCl, pheniramine maleate, ketotifen fumarate, oxymetazoline HCl, naphazoline HCl, pheniramine maleate, moxifloxacin hydrochloride, bromfenac, proparacaine hydrochloride, difluprednate, gatifloxacin, travoprost, bepotastine besilate, gatifloxacin, loteprednol etabonate, timolol ophthalmic, olopatadine hydrochloride, phenylephrine hydrochloride, levofloxacin, ketorolac tromethamine, letanoprost, bimatoprost and BAK free latanoprost. In another aspect, the medicament is selected from the group consisting of Refresh Tears™, Visine Advanced Relief™, Naphcon A™, Sensitive Eyes™, Renu™, Opti-Free™ rewetting drops, Visine A.C.™, Hypo Tears™, Alaway™, Visine L.R.™, Visine™ original, Rohto Cool™, Soothe XP™, Zaditor™, Bausch & Lomb Advanced Eye Relief Redness™, Visine A™, Opcon-A™, Walgreens artificial tears, Visine™ dry eye relief, Advanced Eye Relief Dry Eye™, Opti-free Replenish™, Clear Eyes™ redness relief, Vigamox™, Bromday™, Durezol™, Zymaxid™, Travatan Z™, Tropicamide™, Bepreve™, Zymar™, Lotemax™, Istalol™, Pataday™, AK-Dilate™, Toradol™, Xalatan™, and Lumigan™.

In another aspect, the medicament to be delivered comprises a medicament selected from the group consisting of fluorosilicone acrylate, sodium carboxymethylcellulose, hydroxypropyl methylcellulose, tetrahydrozoline HCl, carboxymethylcellulose sodium, propylene glycol, hypromellose, zinc sulfate, dorzolamide HCl timolol maleate, azithromycin, brimonidine tartrate, nepafenac, brinzolamide, besifloxacin, dorzolamide HCl, prenisone acetate, loteprednol etabonate, tobramycin/dexamethasone, and cyclosporine. In a further aspect, the medicament is selected from the group consisting of Tears Naturale II™, Optimum NWN™, Thera Tears™, Systane Ultra™, GenTear™, Systane Lubricant Eye Drops™, Blink™ tears, Visine Max Redness Relief™, Refresh Optive™, Muro 128™, Systane Balance™, Rohto Hydra™, Rohto Ice™, Walgreens sterile artificial tears, Rohto Arctic™, Clear Eyes™ natural tears lubricant, Similasan™ pink eye relief, Similasan™ allergy eye relief, Cosopt™, AzaSite™ Alphagan P™, Nevanac™, Azopt™, Besivance™ Trusopt™, Alrex™, and Restasis™.

In an aspect, an ophthalmic medicament to be delivered is used to treat glaucoma. In an aspect, a glaucoma medicament is selected from the group consisting of travoprost, timolol ophthalmic, latanoprost, bimatoprost, dorzolamide HCl timolol maleate, brimonidine tartrate, brinzolamide, dorzolamide HCl, and BAK free latanoprost. In a further aspect, a medicament is selected from the group consisting of travoprost, timolol ophthalmic, latanoprost, bimatoprost, and BAK free latanoprost. In another aspect, a medicament is selected from the group consisting of dorzolamide HCl timolol maleate, brimonidine tartrate, brinzolamide, and dorzolamide HCl. In an aspect, a glaucoma medicament is selected from the group consisting of Travatan™, Istalol™, Xalatan™, Lumigan™, Cosopt™, Alphagan P™, Azopt™, and Trusopt™. In another aspect, a medicament is selected from the group consisting of Travatan™, Istolol™, Xalatan™, and Lumigan™. In a further aspect, a medicament is selected from the group consisting of Cosopt™, Alphagan P™, Azopt™, and Dorzolamide HCl™.

In an aspect, the concentration of an active ingredient in a medicament is measured as a percentage of the active ingredient in solution. In an aspect, the concentration of active ingredient ranges from about 0.0001% to about 5%. In another aspect, the concentration of active ingredient in a medicament ranges from about 0.0005% to about 1%. In other aspects, the concentration of active ingredient ranges from about 0.0005% to about 0.0001%, from about 0.0001% to about 0.001%, or from about 0.0005% to about 0.001%. In other aspects, the concentration of active ingredient ranges from about 0.005% to about 0.001% or from about 0.001% to about 0.01%. In another aspect, the concentration of active ingredient ranges from about 0.001% to about 0.5%. In various other aspects, the concentration of active ingredient is selected from the group consisting of about 0.0001%, about 0.0005%, about 0.001%, about 0.0025%, about 0.005%, about 0.01%, about 0.025%, about 0.05%, about 0.1%, about 0.2%, about 0.3%, about 0.4%, about 0.5%, about 0.75%, about 1%, about 1.5%, about 2%, about 2.5%, about 3%, about 4%, and about 5% measured as a percentage of the solution. However, given the lower dosing amounts afforded by the methods of the present disclosure, higher concentrations may be used depending on the intended use. For examples, about 10%, about 20%, about 25%, of the active ingredient in the medicament, measured as a percentage of the solution, may be utilized.

In an aspect, the medicament comprises a medicament selected from the group consisting of between about 0.02% and about 0.03% carboxymethylcellulose sodium, between about 0.4% and about 0.6% carboxymethylcellulose sodium, between about 0.04% and about 0.06% tetrahydrozoline HCl, between about 0.04% and about 0.06% tetrahydrozoline HCl, between about 0.24% and about 0.36% pheniramine maleate, between about 0.02% and about 0.03% ketotifen fumarate, between about 0.028% and about 0.042% ketotifen fumarate, between about 0.02% and about 0.03% oxymetazoline HCl, between about 0.0096% and about 0.0144% naphazoline HCl, between about 0.024% and about 0.036% naphazoline HCl, between about 0.24% and 0.36% pheniramine maleate, between about 0.4% and about 0.6% moxifloxacin hydrochloride, between about 0.072% and about 0.108% bromfenac, between about 0.4% and about 0.6% proparacaine hydrochloride, between about 0.04% and about 0.06% difluprednate, between about 0.4% and about 0.6% gatifloxacin, between about 0.0032% and about 0.0048% travoprost, between about 1.2% and about 1.8% bepotastine besilate, between about 0.24% and about 0.36% gatifloxacin, between about 0.4% and about 0.6% loteprednol etabonate, between about 0.4% and about 0.6% timolol ophthalmic, between about 0.16% and about 0.24% olopatadine hydrochloride, between about 2% and about 3% phenylephrine hydrochloride, between about 0.4% and about 0.6% levofloxacin, between about 0.32% and about 0.48% ketorolac tromethamine, between about 0.004% and about 0.006% letanoprost, and between about 0.024% and about 0.036% bimatoprost.

In an aspect, the medicament comprises a medicament selected from the group consisting of 0.025% carboxymethylcellulose sodium, 0.5% carboxymethylcellulose sodium, 0.05% tetrahydrozoline HCl, 0.5%, tetrahydrozoline HCl, 0.3% pheniramine maleate, 0.025% ketotifen fumarate, 0.035% ketotifen fumarate, 0.025% oxymetazoline HCl, 0.012% naphazoline HCl, 0.03% naphazoline HCl, 0.3% pheniramine maleate, 0.5% moxifloxacin hydrochloride, 0.09% bromfenac, 0.5% proparacaine hydrochloride, 0.05% difluprednate, 0.5% gatifloxacin, 0.004% travoprost, 1.5% bepotastine besilate, 0.3% gatifloxacin, 0.5% loteprednol etabonate, 0.5% timolol ophthalmic, 0.2% olopatadine hydrochloride, 2.5% phenylephrine hydrochloride, 0.5% levofloxacin, 0.4% ketorolac tromethamine, 0.005% letanoprost, and 0.03% bimatoprost.

In another aspect, the medicament to be delivered comprises a medicament selected from the group consisting of between about 0.02% and about 0.3% sodium carboxymethylcellulose, between about 0.04% and about 0.06% tetrahydrozoline HCl, between about 0.4% and about 0.6% carboxymethylcellulose sodium, between about 0.48% and about 0.72% propylene glycol, between about 0.24% and about 0.36% hypromellose, between about 0.2% and about 0.3% zinc sulfate, between about 0.8% and about 1.2% azithromycin, between about 0.08% and about 0.12% brimonidine tartrate, between about 0.08% and about 0.12% nepafenac, between about 0.8% and about 1.2% brinzolamide, between about 0.48% and about 0.72% besifloxacin, between about 1.6% and about 2.4% dorzolamide HCl, between about 0.8% and about 1.2% prenisone acetate, between about 0.16% and about 0.24% loteprednol etabonate, between about 0.32% and about 0.48% tobramycin/dexamethasone, and between about 0.04% and about 0.06% cyclosporine.

In another aspect, the medicament to be delivered comprises a medicament selected from the group consisting of 0.025% sodium carboxymethylcellulose, 0.05% tetrahydrozoline HCl, 0.5% carboxymethylcellulose sodium, 0.6% propylene glycol, 0.3% hypromellose, 0.25% zinc sulfate, 1% azithromycin, 0.1% brimonidine tartrate, 0.1% nepafenac, 1% brinzolamide, 0.6% besifloxacin, 2% dorzolamide HCl, 1% prenisone acetate, 0.2% loteprednol etabonate, 0.4% tobramycin/dexamethasone, and 0.05% cyclosporine.

In an aspect, the medicament to be administered is not water-soluble. In another aspect, the medicament to be administered is poorly water-soluble. In a preferred aspect, the medicament is water-soluble, highly water-soluble, or very highly water-soluble. In an aspect, poorly water soluble is less than 10 ug/mL. In other aspects, water soluble is 10 to 60 ug/mL, highly water soluble is greater than 60 to 120 ug/mL, and very highly water soluble is greater than 120 ug/mL.

In another aspect, the medicament to be administered is formulated in an emulsion or a suspension. In an aspect, the medicament to be delivered comprises difluprednate or loteprednol etabonate. In an aspect, the medicament is Durezol™ or Lotemax™.

As generally understood by those skilled in the art, the listing of an active agent includes medicamently acceptable salts, esters, and acids thereof.

In another aspect, a medicament to be delivered comprises a preservative or other additive acceptable for use in the eye. In an aspect, a medicament comprises 20% or less of a preservative or other additive, or 15% or less, 12% or less, 10% or less, 8% or less, 6% or less, 5% or less, 4% or less, 3% or less, 2% or less, 1% or less, 0.5% or less, 0.4% or less, 0.3% or less, 0.2% or less, 0.1% or less of a preservative or other additive.

In another aspect, the medicament to be delivered comprises a polymeric ingredient. In an aspect, the medicament comprises an additive selected from the group consisting of glycerin, castor oil, carbomer, polyethylene glycol, and polysorbate 80. In an aspect, the concentration of polymer is measured as a percentage of the total solution by weight. In various aspects, the medicament comprises 10% or less of a polymer, 5% or less of a polymer, 4% or less of a polymer, 3% or less of a polymer, 2% or less of a polymer, 1.5% or less of a polymer, 1% or less of a polymer, 0.5% or less of a polymer, 0.4% or less of a polymer, 0.3% or less of a polymer, 0.2% or less of a polymer, 0.1% or less of a polymer, 0.05% or less of a polymer, or no detectable polymer. In various aspects, the medicament comprises 10% or less glycerin, 5% or less glycerin, 4% or less glycerin, 3% or less glycerin, 2% or less glycerin, 1.5% or less glycerin, 1% or less glycerin, 0.5% or less glycerin, 0.4% or less glycerin, 0.3% or less glycerin, 0.2% or less glycerin, 0.1% or less glycerin, 0.05% or less glycerin, or no glycerin.

In various aspects, the medicament may have different tonicity. Tonicity may be measured using a hydrometer. In various aspects, tonicity may range from 0%, or a pure aqueous solution, to 2.5%. In other aspects, tonicity may range from 0.1% to 1%, from 0.5% to 1%, from 0.7% to 1%, from 0.8% to 1%. In further aspects, tonicity of a medicament may be 0.1%, 0.2%, 0.3%, 0.4%, 0.5%, 0.6%, 0.7%, 0.8%, 0.9%, 1%, 1.1%, 1.2%, 1.3%, 1.4%, or 1.5%. In an aspect, the medicament is isotonic with the site of delivery. For example, in various aspects, the medicament may be isotonic with human tears, blood, or eye tissue. It is contemplated that a solution with no active ingredient can be administered, e.g., a wetting agent.

In an aspect, the subject is less than 150 kilograms, 100 kilograms, less than 50 kilograms, less than 25 kilograms, or less than 10 kilograms. In this or other aspects, the subject may be less than 12 or 13 years old. In this or other aspects, the subject could be classified as human, male or female. In this or other aspects, the subject may be an agricultural animal. In this or other aspects, the subject may be non-human.

The viscosity of the medicament to be administered can vary. Viscosity of a medicament formulation can be measured by using a viscometer. In various aspects, viscosity of a medicament at 25° C. ranges from about 0.3 to about 300 cP, from about 0.3 to about 200 cP, from about 0.3 to about 100 cP, from about 0.3 to about 50 cP, from about 0.3 to about 40 cP, from about 0.3 to about 30 cP, from about 0.3 to about 20 cP, from about 0.3 to about 10 cP, from about 0.3 to about 5 cP, from about 0.3 to about 2 cP, from about 0.3 to about 1.5 cP, from about 0.3 to about 1 cP, from about 0.3 to about 0.9 cP, from about 0.3 to about 0.8 cP, from about 0.3 to about 0.7 cP from about 0.3 to about 0.6 cP, from about 0.3 to about 0.5 cP, or from about 0.3 to about 0.4 cP. In various other aspects, viscosity of a medicament to be administered is about 0.4 to about 1.4 cP, about 0.5 to about 1.3 cP, about 0.6 to about 1.2 cP, about 0.7 to about 1.1 cP, or about 0.8 to about 1.0 cP at room 25° C. In various other aspects, viscosity of a medicament at 25° C. is about 0.3 cP, about 0.4 cP, about 0.5 cP, about 0.6 cP, about 0.7 cP, about 0.8 cP, about 0.9 cP, about 1 cP, about 1.1 cP, about 1.2 cP, about 1.3 cP, about 1.4 cP, or about 1.5 cP.

In some aspects, the active agents may exhibit increased stability and/or solubility at acid or alkaline pH and may be centrally administered in such form. In other aspects, a physiologically suitable pH (e.g., in the range of about pH 6.8-8.2, depending on the part of the eye) may be preferred for ophthalmic administration. However, titration to physiological pH may result in solubility and/or stability issues for many active agents. Therefore, it may be preferred in some cases to develop aqueous formulations in which the active agent is formulated with a solubility-enhancing agent or stabilizing excipients at a physiologically suitable pH. If titration is desired, any suitable buffer known in the medicament arts may be used (e.g., phosphate, acetate, glycine, citrate, imidazole, TRIS, MES, MOPS).

Further it may be desirable to maintain physiological isotonicity. For instance, in certain aspects, an osmolality ranging from about 100 to about 1000 mmol/kg, more particularly from about 280 to about 320 mmol/kg may be desired. Any suitable manner of adjusting tonicity known in the pharmaceutical arts may be used, e.g., adjustment with NaCl.

In accordance with certain aspects of the invention, medicament compositions are designed to maximize solubility and stability in ophthalmic applications and under conditions of use for administration to the eye.

1. Solubility Enhancing Agents

Again, in accordance with certain aspects of the invention, formulation active agents in aqueous solutions at physiological pH and tonicity are undertaken. However, to provide adequate solubility to the composition, the use of solubility enhancing agents may optionally be required.

Without intending to be limited by theory, in certain aspects, solubility enhancing agents may utilize their amphiphilic characteristics to increase the solubility of active agents in water. As generally understood by those skilled in the art, a wide variety of solubility enhancing agents that possess both nonpolar and hydrophilic moieties may be employed in connection with the present invention. However, amphiphilic agents possessing stronger hydrophobic character have the potential to interact with cell membranes and produce toxic effects. Therefore, again, without intending to be limited by theory, solubility enhancing agents with minimal hydrophobic character may be preferred in certain aspects within the context of the present invention, as such agents will be well-tolerated.

In addition to minimizing the hydrophobic character of the solubilizing agents employed, toxicity during administration may be reduced if the solubility enhancing agent is readily degraded in a cellular environment. The ability of cells to degrade compounds prevents their accumulation during chronic administration. To this end, the solubility enhancing agents may optionally include chemically-labile ester and ether linkages that contribute to low toxicity, and thereby prevent significant cellular accumulations during chronic administration.

In this regard, in accordance with certain aspects of the invention, the solubility-enhancing agent includes those that can be selected from cyclodextrins, e.g., β-hydroxypropyl-cyclodextrin, sulfobutyl-ether-β cyclodextrin, etc.

In other aspects, the solubility-enhancing agent may be selected from sucrose esters. Such agents are formed of two benign components (sucrose and fatty acids) linked by a highly labile ester bond. Although a readily-degradable linkage is beneficial from a toxicity standpoint, the solubility enhancing agent must be sufficiently robust to maintain its ability to solubilize the active agent during the desired conditions of use.

Generally, certain compositions of the invention may be prepared by formulating the desired amount, which may be a therapeutically-effective amount, of the desired active agent in a suitable solubility enhancing agent. Solubility enhancing agents include, but are not limited to, e.g., cyclodextrins, octylglucoside, pluronic F-68, Tween 20, sucrose esters, glycerol, ethylene glycol, alcohols, propylene glycol, carboxy methyl cellulose, solutol, mixtures thereof, etc. Other solubility-enhancing agents include, but are not limited to, polyethylene glycol (PEG), polyvinlypyrrolidone (PVP), arginine, proline, betaine, polyamino acids, peptides, nucleotides, sorbitol, sodium dodecylsulphate (SDS), sugar esters, other surfactants, other detergents and pluronics, and mixtures thereof. Alternatively, stable multiphase systems could be employed to safely solubilize therapeutics for intrathecal delivery (e.g., liposomes, micro/nano emulsions, nanoparticles, dendrimers, micro/nano spheres).

Any suitable amount of solubility enhancing agent sufficient to solubilize the active agent of interest to the desired concentration may be used. In certain aspects, molar ratios of active agent to solubility-enhancing agent ranging from about 0.5:1 to about 1:10, particularly, about 1:1 to about 1:5, more particularly 1:1 to about 1:2, may be used to achieve adequate solubility of the active agent to the desired concentrations.

2. Stabilizing Excipients

In addition to solubility, the active agent must be sufficiently stable within the composition to withstand hydrolytic and oxidative degradation in order to maintain biological activity during administration. Active agents generally possesses the therapeutic effects observed during conventional administration; the stability of the medicament in the composition prior to central administration is also of importance. To this end, in certain aspects, the compositions of the present invention may further include stabilizing excipients and buffers acceptable for use in the eye.

Considering that oxidation represents a common degradation pathway, in certain aspects, the compositions of the invention may be deoxygenated (e.g., by saturating with nitrogen gas) to minimize the formation of reactive oxygen species that would degrade the active agent during storage. Another method would be to ensure that formulations are stored in a container that does not allow passage of light, thereby minimizing photo-induced degradation. In addition, in accordance with certain aspects of the invention, stabilizing excipients may optionally be used to, e.g., prevent or slow degradation by oxidation and/or hydrolysis of the active agents. For example, vitamin E, methionine, chelators and mannitol may be used to reduce oxidative degradation. Since the rates of many degradation reactions are pH-dependent, such formulations may include any suitable buffering agent known in the art (e.g., phosphate, acetate, glycine, citrate, imidazole, TRIS, MES, MOPS).

Stabilizing excipients useful in the context of the compositions described herein include any medicamently acceptable components which function to enhance the physical stability, and/or chemical stability of the active agent in the compositions of the invention. The medicament compositions described herein may include one or more stabilizing excipients, and each excipient may have one or more stabilizing functions.

In one aspect, the stabilizing excipient may function to stabilize the active agent against chemical degradation, e.g., oxidation, deamidation, deamination, or hydrolysis. In this regard, the stabilizing excipients may optionally be selected from antioxidants, such as ascorbic acid (vitamin C), vitamin E, tocopherol conjugates, tocopherol succinate, PEGylated tocopherol succinate, Tris salt of tocopherol succinate, Trolox, mannitol, sucrose, phytic acid, trimercaprol or glutathione.

The term "effective amount" refers to an amount of an active agent used to treat, ameliorate, prevent, or eliminate the identified ophthalmic condition (e.g., disease or disorder), or to exhibit a detectable therapeutic or preventative effect. The effect can be detected by, for example, chemical markers, antigen levels, or time to a measurable event, such as morbidity or mortality. The precise effective amount for a subject will depend upon the subject's body weight, size, and health; the nature and extent of the condition; and the therapeutic or combination of therapeutics selected for administration. Effective amounts for a given situation can be determined by routine experimentation that is within the skill and judgment of the clinician. Any of the agents can be provided in an effective amount.

For any active agent, the effective amount can be estimated initially either in cell culture assays, e.g., in animal models, such as rat or mouse models. An animal model may also be used to determine the appropriate concentration range and route of administration. Such information can then be used to determine useful doses and routes for administration in humans.

To assist in understanding the present invention, the following Example is included. The experiments described herein should not, of course, be construed as specifically limiting the invention and such variations of the invention, now known or later developed, which would be within the purview of one skilled in the art are considered to fall within the scope of the invention as described herein and hereinafter claimed.

U.S. Application Attorney Docket Number 24591.003-US03, filed concurrently herewith, entitled "Drop-Generating Device" and U.S. Application Attorney Docket Number 24591.003-US02, filed concurrently herewith, entitled "Method and System for Performing Remote Treatment and Monitoring" are also each herein incorporated by reference in their entireties.

EXAMPLE

Table A describes quantification of average droplet size and the maximum number of doses of various medications from individual eyedropper containers. Each experiment is repeated in three trials to calculate a more accurate average droplet size. By taking the volume of individual bottles and dividing it by the average droplet size, the maximum number of doses per eyedropper is calculated.

Column A contains the retail name of medications. In column B, the concentration of active ingredient of medication is listed as a percentage where publically available. Column C contains the name of preservative used in the medication, with column D displaying the percentage of the preservative in the solution. Column E is the manufacturer of the medication and column F is its classification as over-the counter (OTC) or by prescription (Rx). Columns G, H and I represent values from individual trials. The average in Column J is calculated using the values of G, H and I. Every bottle has a unique volume to contain a set amount of medication, which is noted in column K. The value in column K is divided by the average in column J to determine the number of doses possible as noted in Column L.

TABLE A

| Name | med in solution (%) | Preservative | Preserv in solution (%) | Company | RX/OTC | Trial 1 | Trial 2 | Trial 3 | Avg | Bottle Size (ml) | Doses |
|---|---|---|---|---|---|---|---|---|---|---|---|
| Blink tears | | Sodium Chlorate | | Advanced Medical Optics | OTC | 0.041 | 0.046 | 0.041 | 0.0427 | 15 | 352 |
| thera tears (sodium carboxymethylcellulose) | 0.025 | Sodium Perborate | | Advanced Vision Research | OTC | 0.046 | 0.05 | 0.049 | 0.0483 | 30 | 621 |
| Naphcon A (Pheniramine Maleate) | 0.3 | Benzalkonium Chloride | 0.01 | Alcon | OTC | 0.038 | 0.04 | 0.04 | 0.0393 | 15 | 381 |
| Opti-free express rewetting drops | | Polyquad | | Alcon | OTC | 0.036 | 0.038 | 0.038 | 0.037333 | 20 | 535.7 |
| Opti-free Replenish | | Polyquad | 0.001 | Alcon | OTC | 0.026 | 0.027 | 0.029 | 0.0273 | 10 | 366 |
| Systane Balance (propylene glycol) | 0.6 | Polyquad | 0.001 | Alcon | OTC | 0.039 | 0.035 | 0.035 | 0.0363 | 10 | 275 |
| Systane Lubricant Eye drops | | Polyquad | | Alcon | OTC | 0.038 | 0.044 | 0.05 | 0.0440 | 15 | 341 |
| Systane ultra | | Polyquad | 0.001 | Alcon | OTC | 0.047 | 0.047 | 0.049 | 0.0477 | 10 | 210 |
| Tears Naturale II | | Polyquad | 0.001 | Alcon | OTC | 0.057 | 0.056 | 0.06 | 0.0577 | 15 | 260 |
| Refresh optive (Carboxymethylcellulose Sodium) | 0.5 | PURITE | | Allergan | OTC | 0.04 | 0.041 | 0.04 | 0.0403 | 15 | 372 |
| Refresh Tears (Carboxymethylcellulose Sodium) | 0.5 | PURITE | | Allergan | OTC | 0.054 | 0.055 | 0.059 | 0.0560 | 15 | 268 |
| Adv. Eye Relief Dry Eye | | Benzalkonium Chloride | 0.01 | Bausch & Lomb | OTC | 0.027 | 0.028 | 0.03 | 0.0283 | 15 | 529 |
| Adv. Eye relief Redness (Naphazoline HCl) | 0.03 | Benzalkonium Chloride | 0.01 | Bausch & Lomb | OTC | 0.032 | 0.031 | 0.032 | 0.0317 | 15 | 474 |
| Alaway (ketotifen fumarate) | 0.035 | Benzalkonium Chloride | 0.01 | Bausch & Lomb | OTC | 0.036 | 0.034 | 0.035 | 0.0350 | 10 | 286 |
| Muro128 | | | | Bausch & Lomb | | 0.038 | 0.041 | 0.038 | 0.0390 | 15 | 385 |
| Opcon-A | | Benzalkonium Chloride | | Bausch & Lomb | OTC | 0.028 | 0.031 | 0.032 | 0.0303 | 15 | 495 |
| Renu | | Sorbic acid, Disodium edetate | 0.15 and .1 | Bausch & Lomb | OTC | 0.036 | 0.039 | 0.041 | 0.0387 | 15 | 388 |

TABLE A-continued

| Name | med in solution (%) | Preservative | Preserv in solution (%) | Company | RX/OTC | Trial 1 | Trial 2 | Trial 3 | Avg | Bottle Size (ml) | Doses |
|---|---|---|---|---|---|---|---|---|---|---|---|
| Sensitive eyes | | Sorbic Acid and Disodium edetate | .1 and .025 | Bausch & Lomb | OTC | 0.039 | 0.038 | 0.04 | 0.0390 | 30 | 769 |
| Soothe xp | | polyhexa-methylene biguanide | | Bausch & Lomb | OTC | 0.033 | 0.033 | 0.033 | 0.0330 | 15 | 455 |
| Visine A.C. (Tetrahydrozoline HCl) | 0.05 | Benzalkonium Chloride | | Johnson & Johnson | OTC | 0.036 | 0.036 | 0.038 | 0.0367 | 15 | 409 |
| Visine Advanced Relief (Tetrahydrozoline HCl) | 0.05 | Benzalkonium Chloride | | Johnson & Johnson | OTC | 0.038 | 0.043 | 0.041 | 0.0407 | 19 | 467 |
| Visine Dry eye relief | | Benzalkonium Chloride | 0.01 | Johnson & Johnson | OTC | 0.031 | 0.03 | 0.027 | 0.0293 | 15 | 511 |
| Visine L.R. Long Lasting Redness Relief (Oxymetazoline HCl) | 0.025 | Benzalkonium Chloride | | Johnson & Johnson | OTC | 0.036 | 0.036 | 0.032 | 0.0347 | 15 | 433 |
| Visine Max Redness Relief (Tetrahydrozoline HCl) | 0.05 | Benzalkonium Chloride | | Johnson & Johnson | OTC | 0.04 | 0.042 | 0.042 | 0.0413 | 15 | 363 |
| Visine original (Tetrahydrozoline HCl) | 0.05 | Benzalkonium Chloride | | Johnson & Johnson | OTC | 0.034 | 0.034 | 0.034 | 0.0340 | 19 | 559 |
| Visine-A (Pheniramine Maleate) | 0.3 | Benzalkonium Chloride | 0.01 | Johnson & Johnson | OTC | 0.031 | 0.031 | 0.033 | 0.0317 | 15 | 474 |
| Optimum WRW (fluorosilicone acrylate) | | Benzyl Alcohol, Sorbic Acid, Disodium edetate | .1, .05, .1 | Lobob | OTC | 0.055 | 0.052 | 0.058 | 0.055 | 30 | 545.5 |
| Clear eyes natural tears lubricant | | Benzalkonium Chloride | | MedTech Products | OTC | 0.026 | 0.03 | 0.024 | 0.0267 | 15 | 563 |
| Clear eyes Redness relief (naphazoline HCl) | 0.012 | Benzalkonium Chloride | | MedTech Products | OTC | 0.024 | 0.02 | 0.021 | 0.0217 | 30 | 1385 |
| GenTeal (hydroxypropyl methylcellulose) | | GenAqua (Sodium perborate) | | Novartis | OTC | 0.046 | 0.046 | 0.047 | 0.0463 | 15 | 324 |
| Hypo tears | | Benzalkonium Chloride | 0.01 | Novartis | OTC | 0.032 | 0.039 | 0.038 | 0.0363 | 30 | 826 |
| Zaditor (ketotifen fumarate) | 0.025 | Benzalkonium Chloride | 0.01 | Novartis | OTC | 0.033 | 0.032 | 0.034 | 0.0330 | 5 | 152 |
| Rohto arctic (Tetrahydrozoline HCl) | 0.05 | | | Rohto | OTC | 0.035 | 0.03 | 0.034 | 0.0330 | 13 | 394 |
| Rohto Cool (naphazoline HCl) | 0.012 | Benzalkonium Chloride | | Rohto | OTC | 0.037 | 0.033 | 0.03 | 0.0333 | 13 | 390 |
| Rohto Hydra (hypromellose) | 0.3 | | | Rohto | OTC | 0.041 | 0.034 | 0.03 | 0.0350 | 13 | 371 |
| Rohto ice (Zinc Sulfate) | 0.25 | | | Rohto | OTC | 0.035 | 0.03 | 0.038 | 0.0343 | 13 | 379 |
| Similasan allergy eye relief | | Silver sulphate | | Similasan | OTC | 0.044 | 0.044 | 0.046 | 0.0447 | 10 | 224 |
| Similasan pink eye relief | | Silver sulphate | | Similasan | OTC | 0.048 | 0.045 | 0.048 | 0.0470 | 10 | 213 |
| Walgreens artificial tears | | Benzalkonium Chloride | 0.01 | Walgreens | OTC | 0.028 | 0.03 | 0.032 | 0.0300 | 30 | 1000 |
| Walgreens sterile artificial tears (ampules) | | None | 0 | Walgreens | OTC | 0.031 | 0.033 | 0.036 | 0.0333 | | 32 |
| AK-Dilate Phenylephrine Hydrochloride | 2.5 | Benzalkonium Chloride | 0.01 | Akorn | Rx | 0.023 | 0.029 | 0.029 | 0.0270 | 15 | 556 |
| Azopt (brinzolamide) | 1 | Benzalkonium Chloride | 0.01 | Alcon | Rx | 0.039 | 0.039 | 0.039 | 0.0390 | 10 | 256 |
| Nevanac (nepafenac) | 0.1 | Benzalkonium Chloride | 0.005 | Alcon | Rx | 0.04 | 0.039 | 0.043 | 0.0407 | 3 | 74 |
| Pataday (olopatadine hydrochloride) | 0.2 | Benzalkonium Chloride | 0.01 | Alcon | Rx | 0.028 | 0.029 | 0.027 | 0.0280 | 2.5 | 89 |
| Travatan Z (travoprost) | 0.004 | Sofzia | | Alcon | Rx | 0.03 | 0.034 | 0.034 | 0.0327 | 5 | 153 |
| vigamox (moxifloxacin hydrochloride) | 0.5 | None | 0 | Alcon | Rx | 0.039 | 0.045 | 0.046 | 0.0433 | 3 | 69 |

TABLE A-continued

| Name | med in solution (%) | Preservative | Preserv in solution (%) | Company | RX/OTC | Trial 1 | Trial 2 | Trial 3 | Avg | Bottle Size (ml) | Doses |
|---|---|---|---|---|---|---|---|---|---|---|---|
| Ketorolac Tromethamine | 0.4 | Benzalkonium Chloride | 0.006 | Alcon-Falcon | Rx | 0.025 | 0.026 | 0.024 | 0.0250 | 5 | 200 |
| Prednisolone Acetate Ophthalmic suspension | 1 | Benzalkonium Chloride | 0.01 | Alcon-Falcon | Rx | 0.03 | 0.033 | 0.037 | 0.0333 | 5 | 150 |
| Proparacaine Hydrochloride Ophthalmic solution | 0.5 | Benzalkonium Chloride | 0.01 | Alcon-Falcon | Rx | 0.036 | 0.04 | 0.042 | 0.0393 | 15 | 381 |
| Tobramycin and Dexamethasone | 0.4 | Benzalkonium Chloride | 0.01 | Alcon-Falcon | Rx | 0.032 | 0.033 | 0.029 | 0.0313 | 5 | 160 |
| Tropicamide | 1 | Benzalkonium Chloride | 0.01 | Alcon-Falcon | Rx | 0.033 | 0.028 | 0.034 | 0.0317 | 15 | 474 |
| Alphagan P (brimonidine tartrate) | 0.1 | PURITE | 0.005 | Allergan | Rx | 0.041 | 0.042 | 0.05 | 0.0443 | 5 | 113 |
| Lumigan (bimatoprost) | 0.03 | Benzalkonium Chloride | 0.005 | Allergan | Rx | 0.025 | 0.021 | 0.022 | 0.0227 | 5 | 221 |
| Restasis (cyclosporine) (ampules) | 0.05 | None (Sterile) | 0 | Allergan | Rx | 0.025 | 0.023 | 0.025 | 0.0243 | | 30 |
| Zymar (gatifloxacin) | 0.3 | Benzalkonium Chloride | 0.005 | Allergan | Rx | 0.029 | 0.031 | 0.031 | 0.0303 | 5 | 165 |
| Zymaxid (gatifloxacin) | 0.5 | Benzalkonium Chloride | 0.005 | Allergan | Rx | 0.033 | 0.035 | 0.032 | 0.0333 | 2.5 | 75 |
| Alrex (loteprednol etabonate) | 0.2 | Benzalkonium Chloride | 0.01 | Bausch & Lomb | Rx | 0.032 | 0.034 | 0.033 | 0.0330 | 5 | 152 |
| Bepreve (bepotastine besilate) | 1.5 | Benzalkonium Chloride | 0.005 | Bausch & Lomb | Rx | 0.031 | 0.033 | 0.03 | 0.0313 | 5 | 160 |
| Besivance (besifloxacin) | 0.6 | Benzalkonium Chloride | 0.01 | Bausch & Lomb | Rx | 0.036 | 0.041 | 0.04 | 0.0390 | 5 | 128 |
| Lotemax (loteprednol etabonate) | 0.5 | Benzalkonium Chloride | 0.01 | Bausch & Lomb | Rx | 0.029 | 0.031 | 0.031 | 0.0303 | 5 | 165 |
| Dorzolamide HCl Timolol Maleate | | Benzalkonium Chloride | 0.0075 | Hi-tech | Rx | 0.051 | 0.048 | 0.053 | 0.0507 | 10 | 197 |
| AzaSite (azithromycin) | 1 | Benzalkonium Chloride | 0.003 | Inspire | Rx | 0.046 | 0.045 | 0.051 | 0.0473 | 2.5 | 53 |
| Bromday (bromfenac) | 0.09 | Benzalkonium Chloride | | Ista | Rx | 0.046 | 0.04 | 0.038 | 0.0413 | 1.7 | 41 |
| Levofloxacin | 0.5 | Benzalkonium Chloride | 0.005 | Pack | Rx | 0.028 | 0.027 | 0.025 | 0.0267 | 5 | 188 |
| Xalatan (latanoprost) | 0.005 | Benzalkonium Chloride | 0.02 | Pfizer | Rx | 0.022 | 0.023 | 0.026 | 0.0237 | 2.5 | 106 |
| Istalol | 0.5 | Benzalkonium Chloride | 0.005 | Senju | Rx | 0.026 | 0.031 | 0.031 | 0.0293 | 5 | 170 |
| Durezol (difluprednate) | 0.05 | Sorbic Acid | 0.1 | Sirion Therapeutics | Rx | 0.04 | 0.039 | 0.034 | 0.0377 | 5 | 133 |
| Dorzolamide HCl | 2 | Benzalkonium Chloride | 0.0075 | Teva | Rx | 0.036 | 0.04 | 0.04 | 0.0387 | 10 | 259 |
| BAK free Latanoprost | | | | | | 0.035 | 0.033 | 0.034 | 0.0340 | | |

What is claimed:

1. A method of delivering a medicament to an eye of a subject in need thereof as an ejected stream of droplets, the method comprising:
   (a) generating the ejected stream of droplets containing said medicament via a piezoelectric actuated ejection device, said ejector device comprising: a housing; a reservoir disposed within the housing for receiving a volume of ophthalmic fluid; an ejector mechanism comprising an ejector plate having a first surface coupled to a fluid delivery area of the reservoir, the ejector plate including a plurality of openings formed through its thickness; and a piezo electric actuator coupled to a second surface of the ejector plate, the actuator being operable to oscillate the ejector plate at a frequency to thereby generate the ejected stream of droplets upon actuation;
   wherein said ejected droplets have an average droplet ejecting size of between about 20 microns to about 100 microns in diameter and an average initial droplet ejecting velocity between 1 m/s and 10 m/s; and
   (b) delivering said ejected stream of droplets containing said medicament to said eye of the subject in need thereof, wherein between about 85% to about 100% of the ejected mass of said droplets are deposited on the eye.

2. The method according to claim 1, wherein said medicament is delivered in an aqueous droplet solution.

3. The method according to claim 2, wherein said medicament is delivered in an oil/water emulsion droplet.

4. The method according to claim 3, wherein said oil in said oil/water emulsion droplet is a glycerin, a castor oil, or a polysorbate 80 mixture.

5. The method according to claim 1, wherein said medicament is a glaucoma medicament.

6. The method according to claim 1, wherein said medicament is an antibiotic.

7. The method according to claim 1, wherein said average droplet ejecting size is between about 30 microns to about 60 microns.

8. The method according to claim 1, wherein said average initial droplet ejecting velocity is between about 1 m/s to about 4 m/s.

9. The method according to claim 1, wherein said medicament is selected from the group consisting of ranibizumab antibody FAB, VEGF Trap fusion molecule, microplasmin enzyme, macugen pegylated polypeptide, and bevacizumab.

10. The method according to claim 1, wherein said medicament comprises a medicament selected from the group consisting of carboxymethylcellulose sodium, tetrahydrozoline HCl, pheniramine maleate, ketotifen fumarate, oxymetazoline HCl, naphazoline HCl, pheniramine maleate, moxifloxacin hydrochloride, bromfenac, proparacaine hydrochloride, difluprednate, gatifloxacin, travoprost, bepotastine besilate, gatifloxacin, loteprednol etabonate, timolol ophthalmic, olopatadine hydrochloride, phenylephrine hydrochloride, levofloxacin, ketorolac tromethamine, latanoprost, bimatoprost and BAK free latanoprost.

11. The method according to claim 1, wherein said medicament comprises a medicament selected from the group consisting of fluorosilicone acrylate, sodium carboxymethylcellulose, hydroxypropyl methylcellulose, tetrahydrozoline HCl, carboxymethylcellulose sodium, propylene glycol, hypromellose, zinc sulfate, dorzolamide HCl timolol maleate, azithromycin, brimonidine tartrate, nepafenac, brinzolamide, besifloxacin, dorzolamide HCl, prenisone acetate, loteprednol etabonate, tobramycin/dexamethasone, and cyclosporine.

12. The method according to claim 1, wherein said medicament is selected from the group consisting of travoprost, timolol ophthalmic, latanoprost, bimatoprost, dorzolamide HCl timolol maleate, brimonidine tartrate, brinzolamide, dorzolamide HCl, and BAK free latanoprost.

13. A method for providing a solution as an ejected stream of droplets to an eye of a subject in need thereof, the method comprising:
   (a) generating an ejected stream of droplets of said solution via a piezoelectric actuated ejection device, the ejection device comprising: a housing; a reservoir disposed within the housing for receiving a volume of ophthalmic fluid; an ejector mechanism comprising an ejector plate having a first surface coupled to a fluid delivery area of the reservoir, the ejector plate including a plurality of openings formed through its thickness; and a piezoelectric actuator coupled to a second surface of the ejector plate, the actuator being operable to oscillate the ejector plate at a frequency to thereby generate the ejected stream of droplets upon actuation;
   wherein said ejected droplets have an average droplet ejecting size of between about 20 microns to about 100 microns in diameter and an average initial droplet ejecting velocity of between about 1 m/s and 10 m/s; and
   (b) delivering said ejected stream of droplets of said solution to said eye of a subject in need thereof, wherein between about 85% to about 100% of the ejected mass of said droplets are deposited on the eye.

14. The method of claim 13, wherein said solution is an isotonic saline solution.

15. The method according to claim 13, wherein said solution comprises a medicament and said medicament is delivered in an aqueous droplet solution.

16. The method according to claim 13, wherein said solution comprises a medicament and said medicament is delivered in an oil/water emulsion droplet.

17. The method according to claim 16, wherein said oil in said oil/water emulsion droplet is a glycerin, a castor oil, or a polysorbate 80 mixture.

18. The method according to claim 15, wherein said medicament is a glaucoma medicament.

19. The method according to claim 15, wherein said medicament is an antibiotic.

20. The method according to claim 13, wherein said average droplet ejecting size is between about 30 microns to about 60 microns.

21. The method according to claim 13, wherein said average droplet initial ejecting velocity is between about 1 m/s to about 4 m/s.

22. The method according to claim 15, said medicament is selected from the group consisting of ranibizumab antibody FAB, VEGF Trap fusion molecule, microplasmin enzyme, macugen pegylated polypeptide, and bevacizumab.

23. The method according to claim 15, wherein said medicament comprises a medicament selected from the group consisting of carboxymethylcellulose sodium, tetrahydrozoline HCl, pheniramine maleate, ketotifen fumarate, oxymetazoline HCl, naphazoline HCl, pheniramine maleate, moxifloxacin hydrochloride, bromfenac, proparacaine hydrochloride, difluprednate, gatifloxacin, travoprost, bepotastine besilate, gatifloxacin, loteprednol etabonate, timolol ophthalmic, olopatadine hydrochloride, phenylephrine hydrochloride, levofloxacin, ketorolac tromethamine, latanoprost, bimatoprost and BAK free latanoprost.

24. The method according to claim 15, wherein said medicament comprises a medicament selected from the group consisting of fluorosilicone acrylate, sodium carboxymethylcellulose, hydroxypropyl methylcellulose, tetrahydrozoline HCl, carboxymethylcellulose sodium, propylene glycol, hypromellose, zinc sulfate, dorzolamide HCl timolol maleate, azithromycin, brimonidine tartrate, nepafenac, brinzolamide, besifloxacin, dorzolamide HCl, prenisone acetate, loteprednol etabonate, tobramycin/dexamethasone, and cyclosporine.

25. The method according to claim 15, wherein said medicament is selected from the group consisting of travoprost, timolol ophthalmic, latanoprost, bimatoprost, dorzolamide HCl timolol maleate, brimonidine tartrate, brinzolamide, dorzolamide HCl, and BAK free latanoprost.

26. A method of treating glaucoma in a subject in need thereof comprising:
   (a) generating an ejecting stream of droplets containing a medicament for treatment of glaucoma via a piezoelectric actuated ejection device, the ejection device comprising: a housing; a reservoir disposed within the housing for receiving a volume of ophthalmic fluid; an ejector mechanism comprising an ejector plate having a first surface coupled to a fluid delivery area of the reservoir, the ejector plate including a plurality of openings formed through its thickness; and a piezoelectric actuator coupled to a second surface of the ejector plate, the actuator being operable to oscillate the ejector plate at a frequency to thereby generate the ejected stream of droplets upon actuation;
   wherein said droplets have an average droplet ejecting size of between about 20 microns to about 100 microns in diameter and an average initial droplet ejecting velocity of between about 1 m/s and 10 m/s; and
   (b) delivering said ejected stream of droplets containing said medicament to an eye of said subject in need thereof, wherein between about 85% to about 100% of the ejected mass of said droplets are deposited on the eye.

27. The method according to claim 26, wherein said medicament is delivered in an aqueous droplet solution.

28. The method according to claim 27, wherein said medicament is delivered in an oil/water emulsion droplet.

29. The method according to claim 28, wherein said oil in said oil/water emulsion droplet is a glycerin, a castor oil, or a polysorbate 80 mixture.

30. The method according to claim 26, wherein said average droplets ejecting size is between about 30 microns to about 60 microns.

31. The method according to claim 26, wherein said average droplet initial ejecting velocity is between about 1 m/s to about 4 m/s.

32. The method according to claim 26, said medicament is selected from the group consisting of travoprost, timolol ophthalmic, latanoprost, bimatoprost, dorzolamide HCl timolol maleate, brimonidine tartrate, brinzolamide, dorzolamide HCl, and BAK free latanoprost.

33. A method of providing a reduced dosage of a medicament to an eye of a subject in need thereof as an ejected stream of droplets, the method comprising:

(a) generating an ejected stream of droplets containing said medicament via a piezoelectric actuated ejection device, the ejection device comprising: a housing; a reservoir disposed within the housing for receiving a volume of ophthalmic fluid; an ejector mechanism comprising an ejector plate having a first surface coupled to a fluid delivery area of the reservoir, the ejector plate including a plurality of openings formed through its thickness; and a piezoelectric actuator coupled to a second surface of the ejector plate, the actuator being operable to oscillate the ejector plate at a frequency to thereby generate the ejected stream of droplets upon actuation;

wherein said droplets have an average ejecting droplet size of between about 20 microns and about 100 microns in diameter and an average initial droplet ejecting velocity of between 1 m/s and 10 m/s; and (b) delivering said ejected stream of droplets containing said medicament to said eye of said subject in need thereof, wherein between about 85% to about 100% of the ejected mass of said droplets are deposited on the eye, and wherein said droplets provide a total volume of less than 30 μl to said eye.

34. The method of claim 1, wherein said medicament has a viscosity at 25° C. is about 0.3 centipoise (cP) to about 300 cP.

35. The method of claim 34, wherein said viscosity is about 0.3 cP to about 30 cP.

36. The method of claim 1, wherein said medicament is isotonic with human tears or eye tissue.

37. The method of claim 1, wherein said medicament has an osmolality ranging from about 100 milli-osmoles/kilogram (mmol/kg) to about 1000 mmol/kg.

38. The method of claim 37, wherein said medicament has an osmolality ranging from about 280 mmol/kg to about 320 mmol/kg.

* * * * *

UNITED STATES PATENT AND TRADEMARK OFFICE
CERTIFICATE OF CORRECTION

| | | |
|---|---|---|
| PATENT NO. | : 9,087,145 B2 | Page 1 of 1 |
| APPLICATION NO. | : 13/184446 | |
| DATED | : July 21, 2015 | |
| INVENTOR(S) | : Ballou, Jr. et al. | |

It is certified that error appears in the above-identified patent and that said Letters Patent is hereby corrected as shown below:

On Title page, column 1, item 75 under Inventors, line 4, delete "Tsontcho Inachulev," and insert -- Tsontcho Ianchulev, --, therefor.

Signed and Sealed this
First Day of December, 2015

Michelle K. Lee
*Director of the United States Patent and Trademark Office*